(12) United States Patent
MacMahon (10) Patent No.: US 6,203,546 B1
(45) Date of Patent: Mar. 20, 2001

(54) METHOD AND APPARATUS FOR MEDIAL TIBIAL OSTEOTOMY

(76) Inventor: Edward B MacMahon, 15 E. Washington St., Middleburg, VA (US) 20118

( * ) Notice: Subject to any disclaimer, the term of this patent is extended or adjusted under 35 U.S.C. 154(b) by 0 days.

(21) Appl. No.: 09/361,239

(22) Filed: Jul. 27, 1999

(51) Int. Cl.[7] .................................................. A61F 5/00
(52) U.S. Cl. ............................................................ 606/87
(58) Field of Search ................................. 606/87, 88, 90, 606/105; 623/16.11, 17.46, 20.14, 20.17, 20.32, 17.11

(56) References Cited

U.S. PATENT DOCUMENTS

| | | | |
|---|---|---|---|
| 4,421,112 | * 12/1983 | Mains et al. | 606/88 |
| 4,501,268 | * 2/1985 | Comparetto | 606/87 |
| 4,769,040 | * 9/1988 | Wevers | 623/20.32 |
| 4,936,844 | 6/1990 | Chandler et al. | |
| 5,053,039 | * 10/1991 | Hofmann et al. | 606/87 |
| 5,569,250 | 10/1996 | Sarver et al. | |
| 5,620,448 | 4/1997 | Puddu | |
| 5,662,655 | * 9/1997 | Laboureau et al. | 606/75 |
| 5,733,290 | * 3/1998 | McCue et al. | 606/86 |
| 5,749,875 | 5/1998 | Puddu | |
| 5,766,251 | 6/1998 | Koshino | |
| 5,888,223 | 3/1999 | Bray, Jr. | |
| 6,008,433 | * 12/1999 | Stone | 623/20.14 |
| 6,086,593 | * 7/2000 | Bonutti | 606/87 |
| 6,099,531 | * 8/2000 | Bonutti | 606/87 |

* cited by examiner

Primary Examiner—Gene Mancene
Assistant Examiner—Eduardo C. Robert

(57) ABSTRACT

The present invention relates to a method and apparatus for performing a tibial osteotomy to correct misalignment of the knee joint. The apparatus comprises an arcuate implant, a temporary chock and an insertion tray which facilitates the packing of bone growth material in the implant. In the method, preoperative evaluation includes a balancing of the lateral push pull forces through the knee before selecting the implant so that a balanced load through the knee is achieved.

19 Claims, 4 Drawing Sheets

METHOD AND APPARATUS FOR MEDIAL TIBIAL OSTEOTOMY

FIELD OF THE INVENTION

The present invention relates to a method and apparatus for performing a tibial osteotomy to correct misalignment of the knee joint. The invention particularly relates to performing medial tibia osteotomies to correct bowleggedness brought on by degradation in the medial compartment of the knee joint.

BACKGROUND OF THE INVENTION

Medial compartment arthritis of the knee is caused by uncompensated horizontal bending stresses coming from the direction of the medial side of the knee. These stresses produce an overload in the medial compartment with subsequent erosion of the joint surface. Eventually, the bone beneath the joint collapses so that the femur and tibia loose their normal angulation producing a condition commonly known as bow legs. Each person has their own individual set of factors that are responsible for the uncompensated horizontal bending stresses.

Surgical treatment of this arthritis requires that the push-pull forces on the knee first be measured since too little correction will leave the patient bow legged, while too much correction will result in knock knees, the opposite condition. The ideal position is that where the forces through the knee are balanced during weight bearing.

The treatment has two essential goals. The first is to move the angles of the femur and the tibia to a predetermined correct position where the desired distribution of load between the medial and lateral compartments of the knee is obtained. The second is to restore the joint surfaces to proper contact.

Previous attempts to correct the condition involved performing a simple lateral osteotomy in which a wedge of bone is removed from the lateral or outer side of the tibia and the resulting two surfaces are brought together to straighten the leg. However, simply correcting the angle of the tibia relative to the knee and the femur is not sufficient since the angulation of static deformity in a malunited long bone is not equivalent to the angulation of a dynamic deformity at the level of the knee. The knee is a weak cleavage plane in an otherwise rigid column running from the hip to the ankle. An imbalance of the push and pull forces exerted on this plane will produce variable combinations of angulation of the femur as compared to the tibia and each such combination will have a different effect on the surface of the knee joint. The lateral osteotomy procedure ignored the forces affecting the knee as well as the congruency of the convex/concave curvatures of the joint surfaces. Thus, the lateral osteotomy fell into disrepute due to the prevalence of post operative complications such as foot drop due to paralysis of the peroneal nerve and vascular problems in the leg. In addition, the eventual angle in the leg was impossible to predict.

The lateral osteotomy procedure is represented by U.S. Pat. No. 4,936,844, Chandler, et al., which is related to a bone fixation system for securing the osteotomy surfaces together.

As the lateral osteotomy procedure began to fall from favor, total knee replacement became popular as a way to correct arthritic conditions in the knee. Although initially used for cases where arthritis was so extensive that it involved the entire knee, subsequently, the indications for total knee replacement were extended to include patients with bow legs and knock knees in which arthritis was limited to only the medial or lateral compartment.

Although successful, total knee replacement involves significant surgical time as well as post operative recuperation such that a simpler method of dealing with the limited conditions of bowleggedness and knock knees was desired. In the case of bowleggedness, another look at tibial osteotomies was taken with the result being the development of the medial osteotomy in which an osteotomy is made on the medial, or inner, side of the tibia and is opened up and secured, thereby straightening the leg. In early procedures, a graft of bone taken from the patient's iliac crest was inserted into the osteotomy.

Later procedures involve the use of blocks and wedges to hold the osteotomy open. However, these are not without their own deficiencies. For example, U.S. Pat. Nos. 5,620,448 and 5,749,875, Puddu, present a bone plate system for proximal tibial osteotomy in which a tibial wedge is resected and a calibrated wedge tool is employed to open the osteotomy to the desired degree. The bone plate having a small protruding block is secured in place, the block serving as a prop to hold the osteotomy open. The rest of the osteotomy is packed with a bone graft. A significant problem with this system is that the osteotomy is subject to settling or compression within the open wedge since the support obtained from the plate/block combination is limited to a small area of the outer edge of the osteotomy. Settling can result in crumbling of the graft and anterior/posterior and/or lateral rocking through the osteotomy which interferes with the establishment of a secure graft and which places stress on the plate and screws further weakening the area.

In an alternative, U.S. Pat. No. 5,766,251, Koshino, presents a wedge-shaped spacer for use in corrective osteotomies. Although longer than the depth of Puddu's block, the wedge of Koshino is of a relatively narrow width. The result of this is that, like Puddu, the osteotomy is subject to settling on either side of the wedge which can lead to rocking and weakening of the graft through the osteotomy. The wedge has the added disadvantage of being of a length such that it would interfere with a subsequently performed total knee replacement, necessitating an additional procedure to remove the wedge. Furthermore, it has been found that the compression stresses through the osteotomy are such that use of a wedge is substantially limited to correction angles of 10° or less to avoid crumbling of the graft and expression, or squeezing out, of the implant.

In addition to their mechanical disadvantages, these medial procedures, like the lateral osteotomy, fail to take into account the push-pull forces through the knee when calculating the correct placement and corrective angle for the osteotomy. The result of this is that the condition frequently reasserts itself after a relatively short period of time. The longevity of the medial osteotomy procedure and the knee joint is dependent upon achieving congruence of the joint surface. This includes establishing an even distribution of load between the medial and lateral compartments, establishing the direction of stresses on the joint in as vertical an orientation as possible, utilizing all available contact area in the joint to spread the load, and maintaining ligament tension to prevent rattling of the joint during motion. Only by establishing and balancing the push-pull forces will the osteotomy be successful over the long term to improve unicompartmental arthritis of the knee and to correct tibial displacement.

SUMMARY OF THE INVENTION

The present invention overcomes the disadvantages of the prior art and provides an improved method and apparatus for performing tibial osteotomy procedures. The apparatus of the present invention comprises an improved implant which provides superior support within the osteotomy, templates and osteotome guides for performing the osteotomy, and an insertion tool which provides a means to support the implant for insertion and to allow packing of bone chips or artificial bone growth material around the implant prior to insertion. In the method there is provided a means to perform the osteotomy in such a way that the push and pull forces through the knee are determined and balanced resulting in a more accurate correction of the underlying cause of the condition.

The invention provides an implant usable in medial tibial osteotomy and comprising an arcuate block defined by a convex peripheral wall, a concave inner wall, a distal surface and a proximal surface, the proximal surface being relieved to form a reservoir therein capable of receiving bone growth material. In an alternative embodiment for use in osteotomies where the angle of correction is 10° or less, the implant is provided as a wedge wherein the distal surface is flat and the proximal surface has a downward pitch from the peripheral wall to the inner wall.

The invention further provides an apparatus for use in performing a medial tibial osteotomy comprising:

a) an arcuate implant defined by a convex peripheral wall and a concave inner wall joining at spaced ends, a distal surface and a proximal surface, the implant having an arcuate reservoir formed in the proximal surface for receiving bone growth material, the reservoir being open to the proximal surface and having at least one discrete opening extending through the implant to the distal surface;

b) an osteotomy chock comprising a block corresponding to the peripheral wall height of the implant; and c) an insertion tray comprising means to receive and hold the implant for preparation and insertion into the osteotomy.

In addition, the invention provides a method of performing an osteotomy in a long bone to correct a joint displacement using an arcuate implant defined by a convex peripheral wall and a concave inner wall joining at spaced ends, a distal surface and a proximal surface, the implant having a reservoir for receiving bone growth material, the reservoir being exposed at the proximal and distal surface, a chock comprising a block corresponding to the peripheral wall height of the implant, and an insertion tray comprising means to receive and hold the implant for preparation and insertion into an osteotomy; the method comprising the steps of:

a) conducting a preoperative evaluation of forces through a joint to establish a position where the horizontal forces acting on the joint are zero so the remaining forces are vertical and the load through the joint is properly distributed;

b) determining the required angle of correction and selecting the arcuate implant having the required peripheral wall height;

c) forming an incision over the osteotomy site and retracting soft tissues and ligaments;

d) cutting a horizontal osteotomy in the bone leaving a portion of cortical bone opposite the osteotomy to serve as a hinge;

e) opening the osteotomy and inserting the chock as a temporary hold;

f) placing the implant on the insertion tray and packing the reservoir and space between the spaced ends with bone growth material; and g) using the tray to insert the implant and packed bone growth material into the osteotomy such that the spaced ends of the implant are innermost and the peripheral wall is substantially flush with the bone surface at the osteotomy;

whereby the implant maintains the bone at the correct angle while bone growth occurs to close the osteotomy.

It is therefor an object to provide a method and apparatus for performing tibial osteotomy.

It is a further object to provide a method and apparatus which will correct lateral knee displacement brought about by unbalanced push and pull forces through the knee.

It is a still further object to provide a method and apparatus which provides improved support through the osteotomy.

Further objects and advantages will become clear from the following drawings and description.

DETAILED DESCRIPTION OF THE INVENTION

Figure 1:
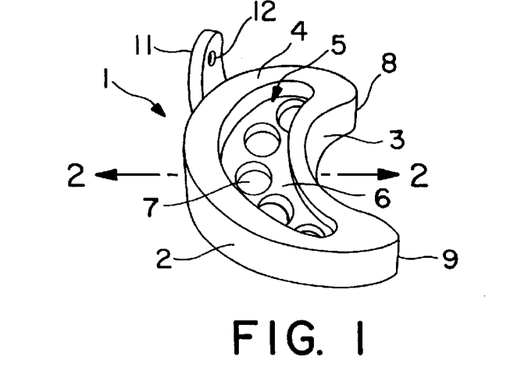
FIG. 1 shows the implant of the present invention.
Figure 2:
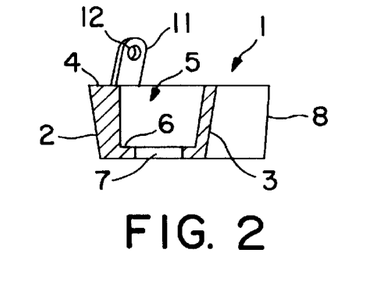
FIG. 2 is a cross section taken along line 2—2 of FIG. 1.
Figure 3:
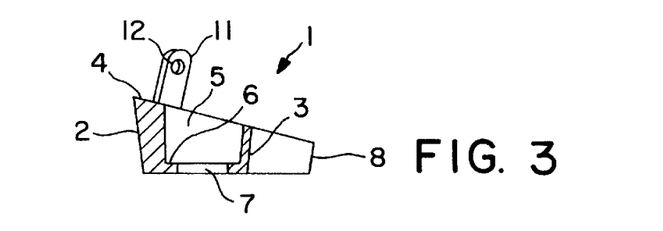
FIG. 3 is a cross section taken along line 2—2 of FIG. 1 showing an alternative embodiment of the implant.
Figure 10:
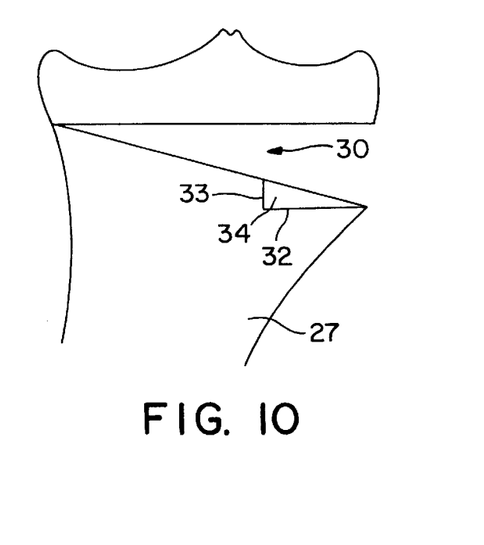
FIG. 10 is a front view of the knee joint with the osteotomy open preparatory to receiving the implant.

In the preferred embodiment shown in FIG. 1, the implant 1 is an arcuate block having a convex peripheral or medial wall 2 and a concave inner or lateral wall 3 joining at spaced ends 8 and 9. The overall arc of the medial wall 2 between ends 8 and 9 corresponds substantially to the medial surface of the tibia at a location approximately 2 cm below the plane of the knee joint. As shown in FIGS. 2 and 3 the medial wall 2 preferably has an outward flare to correspond to the normal flare of the upper tibia which is evident in FIGS. 10 and 11.

The proximal or upper surface 4 of the implant 1 is relieved in an arc corresponding to the arc of the implant 1 to provide a reservoir 5 which is capable of receiving bone chips or other bone growth material. The floor 6 of the reservoir 5 is pierced by a plurality of openings 7 which provide means whereby bone can grow through from the distal or lower surface of the implant when placed in the osteotomy.

Figure 7:
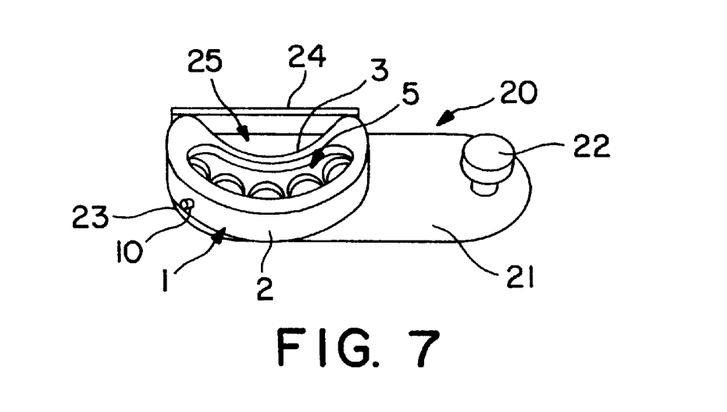
FIG. 7 shows the wedge implant on the insertion tray of FIG. 6.
Figure 11:
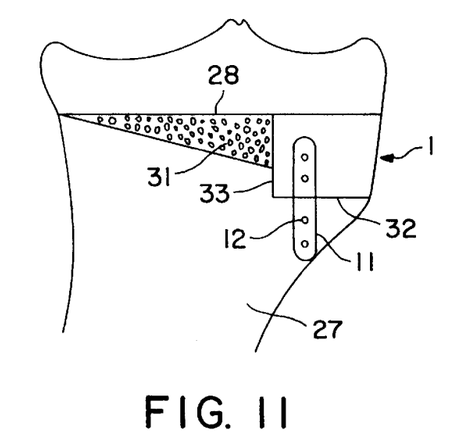
FIG. 11 shows a completed osteotomy with the first embodiment of the implant.
Figure 12:
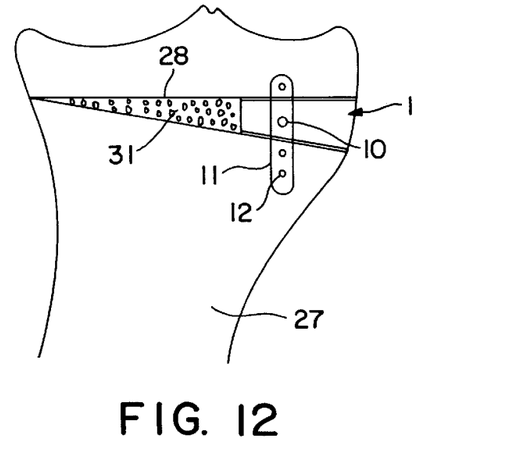
FIG. 12 shows a completed osteotomy with the second embodiment of the implant.

At a location on the medial wall 2 so as not to interfere with the medial collateral ligament, the implant 1 is provided with means to secure it to the tibia so as to prevent inadvertent expression from the osteotomy until secure bone growth has occurred. Such means may comprise a simple tapped and threaded hole 10, as shown in FIG. 7, to which a cortical plate may be attached by a screw, or it may comprise an integral tab 11 as shown in FIGS. 1–3. Tab 11 may extend above the implant 1 as shown in FIGS. 1–3, or below the implant as shown in FIG. 11, or both above and below as shown in FIG. 12. Tab 11 is predrilled with at least one hole 12 to accommodate a fixation screw 13 whereby the implant 1 is secured to the tibia.

In a first embodiment, shown in FIGS. 1 and 2, implant 1 has a constant overall thickness which corresponds to the maximum height of the osteotomy at the medial surface of the tibia needed to achieve the desired angle of correction. Although this embodiment can be used in osteotomies of any angle, it is particularly suitable for angles of correction greater than 10° and most particularly for angles of correction greater than 10°. For angles of correction which are substantially 10° or less, a second embodiment of the implant 1, shown in FIG. 3, is provided. In this embodiment, the proximal surface 4 of the implant 1 has a downward pitch from the peripheral wall 2 to the inner wall 3 and ends 8 and 9 which corresponds to the angle of correction.

Figure 4:
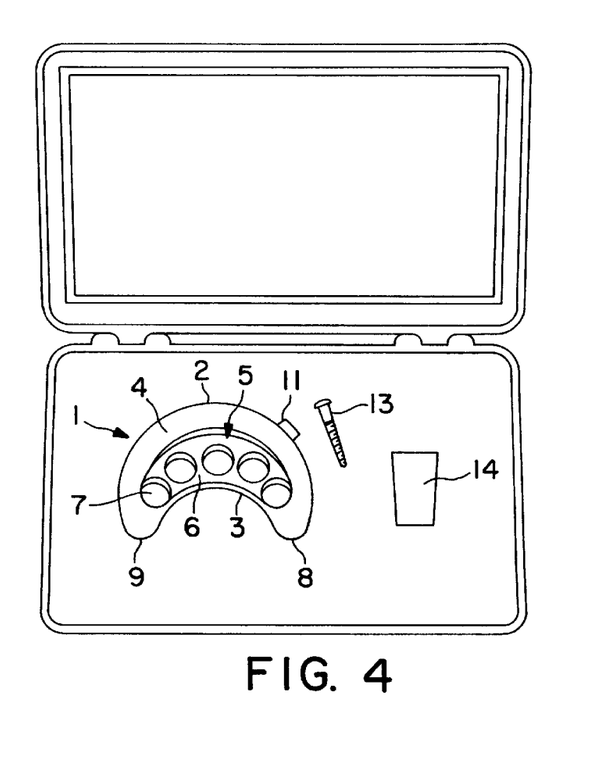
FIG. 4 shows a kit comprising a matched implant, chock and fastening screw.

Associated with implant 1 is a chock 14 which has a thickness corresponding to the peripheral wall height of the implant 1. In the case of the second embodiment of the implant, chock 14 may also have a wedge angle corresponding to that of the implant 1. The chock 14 serves as a temporary block to hold the osteotomy open while the implant 1 is prepared and inserted. To ensure that a surgeon has a chock 14 and an implant 1 of the same size or angle, the implant., 1, screw 13 and chock 14 are preferably provided in a set as shown in FIG. 4.

Figure 5:
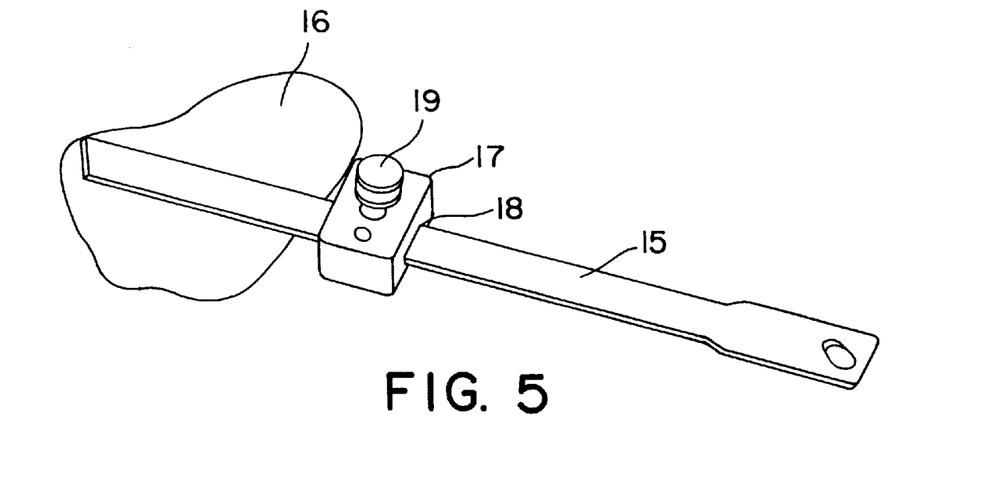
FIG. 5 shows a tibia template and depth stop in combination with an osteotome.

The apparatus for performing the medial tibial osteotomy includes items for use with an osteotome to ensure that the osteotomy is cut to the correct depth. These items are shown in FIG. 5 in combination with a standard Moreland osteotome 15 and consist of a tibial template 16 and a depth stop 17. The template 16 corresponds in size and shape to the cross-section of the tibia at the location of the osteotomy. A plurality of templates 16 can be provided in a variety of sizes in which case the surgeon will select a template 16 closest to the actual dimension of the patient's tibia. Alternatively, templates 16 can be custom manufactured based on X-ray, CT scan or MRI measurements taken during the preoperative analysis phase of the method.

Depth stop 17 comprises a block having a slot 18 therethrough which is sized to accommodate the blade of the osteotome 15 so that the depth stop 17 is slidably positionable along the blade. A set screw 19 is provided in the depth stop 17 and extends through the slot 18. The set screw 19 is tightened against the osteotome 15 to secure the depth stop 17 in the desired location.

Template 16 is used in the manner shown in FIG. 5 to set the position of the depth stop 17 on the osteotome 15 so that the surgeon has an accurate guide for the correct depth to cut the osteotomy without cutting through the lateral cortex of the tibia. By laying the osteotome 15 on the template 16, the depth stop 17 can be slid to the point where it contacts the edge of the template 16 and the set screw 19 tightened to secure the depth stop in place. In this manner, when the surgeon is cutting the osteotomy, the depth stop 17 will contact the surface of the tibia when the cut has been made to the correct depth. By loosening the set screw 19 and repositioning the depth stop 17 relative to the template 16, the osteotome 15 can be reset for different depths of cut through the tibia.

Figure 6:
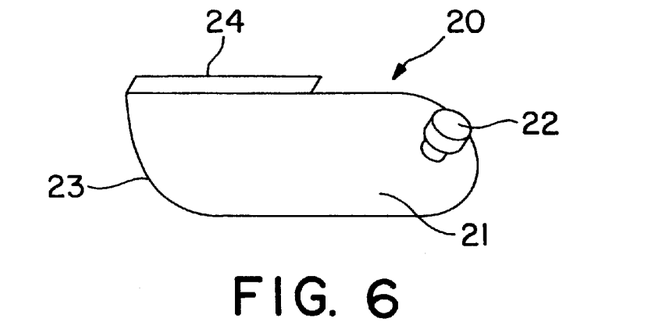
FIG. 6 shows the insertion tray.

FIGS. 6 and 7 illustrate a tray 20 which is used to prepare and insert the implant 1 into the osteotomy. Tray 20 consists of an elongated plate 21 having a first end provided with a manipulation knob 22 and a second end 23 which is formed to substantially match the curvature of the medial wall 2 of the implant 1. Along the lateral edge of the plate 21 is an upturned lip 24, against which the ends 8 and 9 of the implant 1 butt. Tray 20 provides a support for the implant 1 during packing of the reservoir 5 with bone chips and provides a base under the openings 7 to prevent the bone chips from falling through. In addition, lip 24 forms a temporary wall spanning the space between ends 8 and 9 of the implant 1, thereby closing the uncontained volume 25 which is defined by the lateral wall 3 of the implant 1. This permits that volume 25 to also be packed with bone chips or the like such that a more complete filling of the osteotomy with bone chips or artificial bone growth material is accomplished. Following packing of the implant reservoir 5 and the volume 25, the tray 20 provides a tool whereby the implant and the bone packing can be easily inserted into the osteotomy after which the tray 20 is removed simply by sliding it out from under the implant 1.

The implant 1 is specifically designed in a plurality of shapes and sizes to fit into the osteotomy which is precalculated on the basis of preoperative evaluation and computer analysis of the conditions of the knee. The implant is easily and quickly inserted after a horizontal cut is made in the upper tibia. The opening created by the osteotomy is filled with cancellous bone chips, artificial bone growth material or bone graft. Because of its arcuate shape corresponding to the dimensions of the medial section of the tibia, the implant provides sufficient support to the osteotomy in both the anterior-posterior plane and the medial plane and thus solves the problem of settling and resultant crumbling of the graft. The arcuate shape also provides anterior/posterior support within the osteotomy thereby eliminating the rocking through the osteotomy which is encountered with other apparatus and methods. In addition, the arcuate shape provides this support through the osteotomy without extending into the intramedullary space of the tibia; rather, the concave lateral wall 3 of the implant 1 leaves the intramedullary space free such that, if a total knee replacement becomes necessary at a later date, the tibial component of a total knee apparatus can be readily implanted without having to first remove the medial osteotomy implant 1. Furthermore, the implant 1 serves as a receptacle for bone material and a block to prevent the expression of bone material packed into the osteotomy, thereby improving the growth of new bone throughout the osteotomy.

The method of the medial osteotomy using the herein described apparatus begins with a preoperative evaluation of the patient, a full length standing X-ray of the leg is taken with a 10 cm metal rod taped to the medial side of the knee. This provides a true length of the mechanical axis of the femur and tibia as well as true width of the upper tibia and lower femur. Also from this X-ray, the angle that the long axis of the tibia makes with the vertical is measured. From a lateral X-ray, the slope of the joint surface of the upper tibia is measured and laxity of the knee is determined from a set of varus/valgus stress X-rays. These X-rays are scanned and their outlines are digitized for a preoperative osteotomy simulation. In addition, the length of the mechanical axis of the femur and the distance from the center of the knee to the subtalar joint is measured and normalized to the length of the 10 cm rod.

Using this data, the deformity of the lower extremity is classified as either Type I or Type II. In a Type I deformity, the femur is in normal alignment while the tibia is in varus so that the foot is medially displaced. In Type II, the knee is laterally displaced so that both the femur and the tibia are angled in the lateral direction. As part of the preoperative measurements, the torque strengths of the abductor and adductor muscles, the quadriceps and hamstring muscles are determined.

Figure 8:
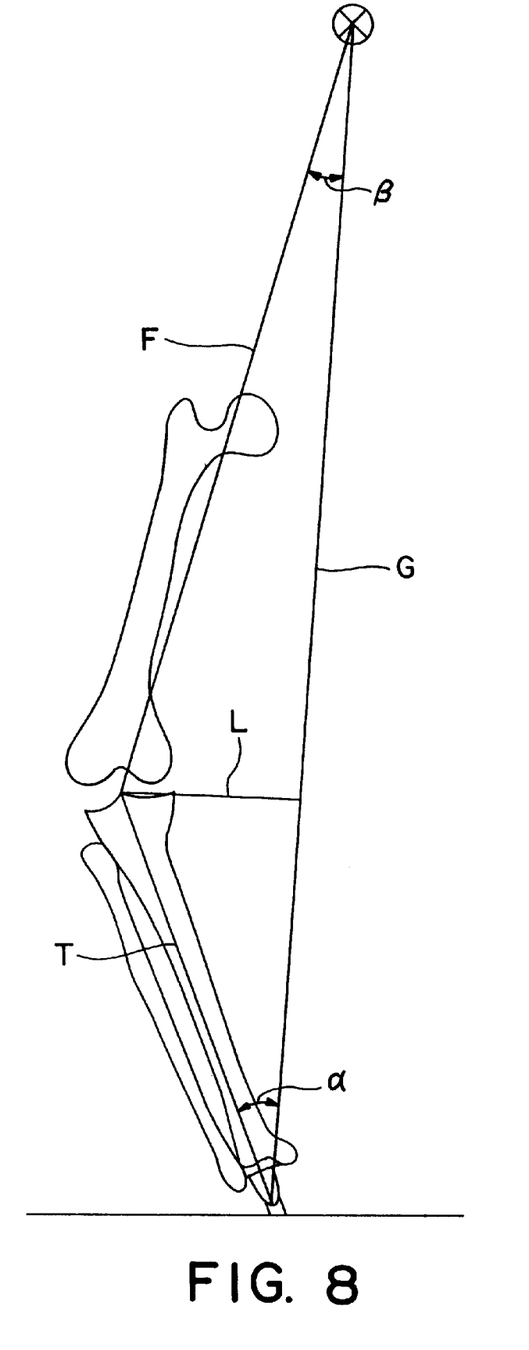
FIG. 8 is a diagram representing the lateral thrust on the knee during weight bearing.
Figure 9:
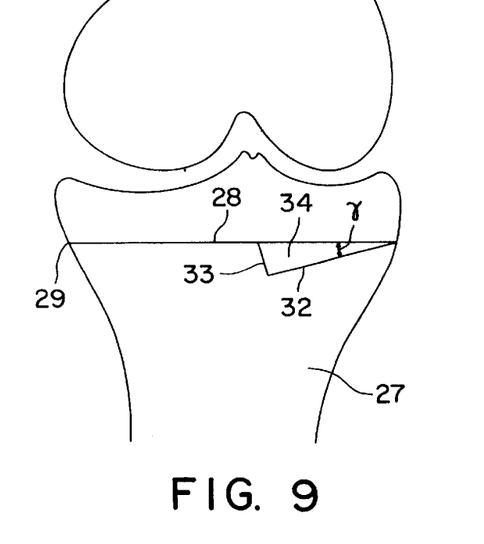
FIG. 9 is a front view of the knee joint before the tibial implant showing the location of the osteotomy cuts.

Gait studies are made with the patient walking over a force plate to determine the magnitude and direction of the ground reaction force. From this data, the horizontal bending moment of the knee is calculated together with the lateral push and pull forces exerted through the knee by the leg muscles. FIG. 8 is a diagram representing the lateral thrust on the knee during weight bearing. Lateral thrust is calculated using commercially available software for gait studies of moments, forces and moment arms. In particular, line G represents the ground reaction force which is obtained from the data of the gait studies. Lines F and T represent the mechanical axes of the femur and tibia respectively and intersect at the knee. Line L connects the intersection point of lines F and T at a right angle to Line G and its length represents the value of the lateral thrust or push which is produced by the body weight during walking and which forces the knee outward. Since the lateral thrust or push caused by body weight acting on the knee works against the pulling force of the adductor muscles, that pulling force must be accounted for. Thus, the true lateral thrust is determined by subtracting the measured adductor torque from the calculated lateral thrust.

From these measurements, it is possible to determine the correct position of the knee where the lateral thrust is zero. Using the scanned X-ray images in a computer simulation, the femur and tibia are manipulated into a position with the lateral femoral condyle correctly seated into the lateral compartment and a simulated osteotomy is performed to determine the best fit contact in the joint. The geometries of the simulated opening are measured to determine the angle of correction and the appropriate implant or implant kit is selected. If the geometries require that the upper tibia be rotated in the side plane or sagittal view, this can be accomplished using a modified implant which is shaped to provide the desired rotation.

In the preferred surgical procedure shown in FIGS. 9–12, following the preoperative analysis, the knee is arthroscopically examined for any damage and is debrided. A 3 cm horizontal incision is made at a level 2 cm below the medial joint line and beginning at the medial edge of the tibia 27. The pes anserinus and medial collateral ligament are retracted and elevated off the tibia 27. The bone is exposed and an alignment jig/saw guide is placed on the front of the leg so that the flat area of the upper part of the jig is level with the incision. An oscillating saw is placed level with the flat surface of the jig and a cut 28 is made in the upper tibia from front to back at the 2 cm level. Using a thin osteotome, such as a Moreland osteotome, the cut 28 is extended medially with care being taken to avoid damaging the medial collateral ligament. The cut 28 is then extended laterally up to but not through the lateral cortex 29.

To ensure a proper depth of cut 28, template 16 corresponding to the cross section of the upper tibia at the level of 2 cm below the joint line is provided as a guide. Using the template 16, the surgeon is able to locate and fix the depth stop 17 on the osteotome as previously described at the point corresponding to the desired depth of the cut 28.

Where the angle of correction is such that the wedge embodiment of implant 1 is suitable, the osteotomy 30 is opened up with valgus pressure on the leg and the chock 14, which is matched to the implant 1 to be used, is inserted at the medial edge to hold the osteotomy open. With the chock 14 in place, cancellous bone, artificial bone material, or bone graft 31 is packed into the lateral side of the osteotomy 30. The implant 1 is prepared by placing it on the insertion tray 20 and packing the reservoir 5 with bone chips. In addition, the uncontained volume 25 on the lateral side of the implant 1 is similarly packed with bone chips, the upturned lip 24 of the tray 20 providing a temporary wall to retain the chips. Preferably, the bone chips are of cancellous bank bone and are in the size range of 1000–4000 microns. However, artificial bone materials may also be used as well as direct bone grafts. In addition, both natural and artificial bone growth enhancement materials, such as bone morphogenic protein, can be added to the chips to promote healing and bone growth.

With the implant 1 thus prepared, the chock 14 is removed while the osteotomy 30 is held open with manual pressure. The tray 20 with the implant 1 and bone chips thereon is inserted into the medial side of the osteotomy 30. Manual pressure is released and the tray 20 is removed by sliding it out from under the implant 1. Any remaining voids on the lateral side of the implant 1 are packed with bone chips. An osteotomy performed in this manner is shown in FIG. 12.

Where the first embodiment of the implant 1 is to be used, for example in cases where the angle of correction is 10°–15° or greater, the first cut 28 is made in the manner described. Thereafter, to provide a proper floor in the distal surface of the osteotomy 30 to receive the implant 1, a second cut 32 is made at a downward angle from the medial surface of the tibia 27. The angle γ of this cut corresponds to the angle of correction of the osteotomy as determined by the preoperative evaluation. Using the osteotome 15 and depth stop 17, the second cut is made to a depth corresponding to the depth of implant 1. A third cut 33 is made in the anterior/posterior direction at the end of the second cut 32 and 90° thereto resulting in a wedge of bone 34 which is removed from the osteotomy 30 and reserved. Thus, when the osteotomy 30 is opened to the angle of correction as in FIG. 11 and wedge 34 is removed, the second cut 32 provides a substantially horizontal floor which is parallel to first cut 28 and spaced therefrom a distance corresponding to the thickness of implant 1. As before, the lateral side of the osteotomy 30 is packed with cancellous bone, artificial bone material or bone graft 31 and implant 1 is prepared and inserted as described. Bone wedge 34 can be used as part of the graft material 31, for example it can be used to fill reservoir 5 or volume 25.

To ensure that the implant 1 is not expressed from the osteotomy, it is preferably secured by means of a small screw 13 driven into the tibia through the fixation tab 11. Alternatively, a bone plate can be attached to the tibia over the medial surface of the implant 1 to hold it in place during healing and bone growth.

The medial collateral ligament, which was previously separated, is reattached to the tibia. The medial wall 2 of the implant is preferably coated with a layer of hydroxyapatite or other bone material to facilitate attachment of the ligament across the implant 1.

Finally, the soft tissues are closed and the patient is fitted with a knee immobilizer brace for a period of time to permit undisturbed healing of the osteotomy.

Although described in connection with a single osteotomy, the apparatus and method of the present invention are applicable to conditions where the required angle of correction is so great that a single osteotomy is difficult and has the potential of not healing properly. Under those conditions, it is within the scope of the present invention to apportion the correction between two osteotomies. Thus, for example, a 20° correction may be achieved by performing two 10° osteotomies using the appropriate size implant in each one. Similarly, a 15° correction may be apportioned between a 10° and a 5° osteotomy. Where two osteotomies are performed, it is preferred that one be at the optimum site of approximately 2 cm below the medial joint line while the other be at a location below the tibial tubercule. In each location the advantages of the implant and the method over the prior art are obtained.

The above description and drawings illustrate the preferred embodiments of the present invention and it is understood that many variations and modifications will be evident to those skilled in the art and may be carried out without departing from the spirit and scope of the present invention.

What is claimed is:

1. An implant usable in medial tibial osteotomy comprising an arcuate block defined by a convex peripheral wall, a concave inner wall, a distal surface and a proximal surface, the peripheral wall having an outward flare from the distal surface to the proximal surface, the proximal surface being relieved to form a reservoir therein capable of receiving bone growth material.

2. The implant of claim 1 further comprising tibial attachment means on the peripheral wall.

3. The implant of claim 2 wherein the tibial attachment means comprises means to which a bone plate is attached.

4. The implant of claim 2 wherein the tibial attachment means comprises a tab extending from the peripheral wall above the proximal surface of the implant and having means to receive a screw therethrough whereby the tab is fixable to the tibia above the osteotomy.

5. The implant of claim 2 wherein the tibial attachment means comprises a tab extending from the peripheral wall below the distal surface of the implant and having means to receive a screw therethrough whereby the tab is fixable to the tibia below the osteotomy.

6. The implant of claim 2 wherein the reservoir is arcuately shaped in common with the implant and includes at least one opening extending from the reservoir through the distal surface of the implant.

7. An apparatus for use in performing a medial tibial osteotomy comprising:
    a) an arcuate implant defined by a convex peripheral wall and a concave inner wall joining at spaced ends, a distal surface and a proximal surface, the implant having an arcuate reservoir formed in the proximal surface for receiving bone growth material, the reservoir being open to the proximal surface and having at least one discrete opening extending through the implant to the distal surface;
    b) an osteotomy chock comprising a block corresponding to the peripheral wall height of the implant; and
    c) an insertion tray comprising means to receive and hold the implant for preparation and insertion into the osteotomy.

8. The apparatus of claim 7 wherein the insertion tray comprises,
    a) a planar surface capable of receiving the implant thereon and providing a surface under the at least one discrete opening;
    b) an upstanding lip along one edge of the planar surface against which the spaced ends of the implant butt whereby the concave inner wall is opposite the lip and together with the lip defines a substantially semicircular space capable of receiving bone growth material; and
    c) a manual manipulation means.

9. The apparatus of claim 8 further comprising a template corresponding to a horizontal cross section of the tibia at the osteotomy location.

10. The apparatus of claim 9 further comprising a depth stop for placement on an osteotome and comprising a block having a horizontal slot therethrough, said slot being of a size to slidably receive the osteotome, whereby the depth stop is variably positionable along the osteotome, and a set screw threadably received in the block and extending into the slot to contact the osteotome, the set screw being tightenable against the osteotome to clamp the depth stop in place thereon.

11. The apparatus of claim 10 provided as a kit for performing a medial tibial osteotomy.

12. A method of performing an osteotomy in a long bone to correct a joint displacement using an arcuate implant defined by a convex peripheral wall and a concave inner wall joining at spaced ends, a distal surface and a proximal surface, the implant having a reservoir for receiving bone growth material, the reservoir being exposed at the proximal and distal surface, a chock comprising a block corresponding to the peripheral wall height of the implant, and an insertion tray comprising means to receive and hold the implant for preparation and insertion into an osteotomy; the method comprising the steps of:
    a) conducting a preoperative evaluation of forces through a joint to establish a position where the horizontal forces acting on the joint are zero so the remaining forces are vertical and the load through the joint is properly distributed;
    b) determining the required angle of correction and selecting the arcuate implant having the required peripheral wall height;
    c) forming an incision over the osteotomy site and retracting soft tissues and ligaments;
    d) cutting a horizontal osteotomy in the bone leaving a portion of cortical bone opposite the osteotomy to serve as a hinge;
    e) opening the osteotomy and inserting the chock as a temporary hold;
    f) placing the implant on the insertion tray and packing the reservoir and space between the spaced ends with bone growth material; and
    g) using the tray to insert the implant and packed bone growth material into the osteotomy such that the spaced ends of the implant are innermost and the peripheral wall is substantially flush with the bone surface at the osteotomy;
    whereby the implant maintains the bone at the correct angle while bone growth occurs to close the osteotomy.

13. The method of claim 12 further comprising packing bone growth material into the inner portion of the osteotomy prior to insertion of the implant.

14. The method of claim 13 further comprising fixing the implant to the bone by means of a fixation tab attached to the peripheral wall of the implant and extending over the surface of the bone, the tab having means to receive a screw therethrough.

15. The method of claim 14 wherein the bone is a tibia and the joint displacement is a lateral displacement of the knee.

16. The method of claim 15 wherein the osteotomy is performed from the medial side of the tibia at a location approximately 2 cm below the tibial joint surface and the peripheral wall of the implant has a curvature substantially equal to that of the medial surface of the tibia.

17. The method of claim 16 wherein the preoperative evaluation comprises establishing a value for lateral thrust exerted on the knee by the downward force of body weight as modified by pull exerted by adductor muscles and applying that value in a simulated osteotomy to determine the required wedge angle of the implant.

18. The method of claim 17 wherein the lateral thrust through the knee is determined from gait analysis and is calculated from measurements of body weight and angular displacement of tibial and femoral mechanical axes from vertical.

19. The method of claim 17 wherein the preoperative evaluation further comprises conducting computer simulation of an osteotomy using scanned and digitized images from X-rays of the knee.

* * * * *